United States Patent
Ishikawa

(10) Patent No.: US 10,368,895 B2
(45) Date of Patent: Aug. 6, 2019

(54) METHOD FOR REPLACEMENT ARTHROPLASTY

(71) Applicant: OLYMPUS CORPORATION, Tokyo (JP)

(72) Inventor: Manabu Ishikawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 367 days.

(21) Appl. No.: 15/085,521

(22) Filed: Mar. 30, 2016

(65) Prior Publication Data

US 2017/0172610 A1    Jun. 22, 2017

Related U.S. Application Data

(60) Provisional application No. 62/268,931, filed on Dec. 17, 2015.

(51) Int. Cl.
| | | |
|---|---|---|
| A61B 17/32 | (2006.01) | |
| A61B 17/16 | (2006.01) | |
| A61F 2/32 | (2006.01) | |
| A61F 2/38 | (2006.01) | |
| A61F 2/46 | (2006.01) | |
| A61F 2/30 | (2006.01) | |

(52) U.S. Cl.
CPC .. *A61B 17/320068* (2013.01); *A61B 17/1668* (2013.01); *A61B 17/1675* (2013.01); *A61F 2/32* (2013.01); *A61F 2/389* (2013.01); *A61F 2/3859* (2013.01); *A61F 2/461* (2013.01); *A61F 2/4607* (2013.01); *A61B 2017/320084* (2013.01); *A61B 2217/005* (2013.01); *A61B 2217/007* (2013.01); *A61F 2002/30428* (2013.01); *A61F 2002/4635* (2013.01)

(58) Field of Classification Search
CPC ........ A61B 17/320068; A61B 17/1675; A61B 17/1668; A61B 2017/320084; A61F 2/32; A61F 2/3859; A61F 2/389; A61F 2/461; A61F 2/4607; A61F 2002/30428
See application file for complete search history.

(56) References Cited

U.S. PATENT DOCUMENTS

| | | | | |
|---|---|---|---|---|
| 3,990,452 A | * | 11/1976 | Murry | A61B 17/22012 606/169 |
| 4,399,813 A | * | 8/1983 | Barber | A61B 17/1615 606/100 |
| 4,787,383 A | * | 11/1988 | Kenna | A61B 17/154 606/80 |
| 4,865,607 A | * | 9/1989 | Witzel | A61F 2/38 623/20.32 |
| 4,936,863 A | * | 6/1990 | Hofmann | A61F 2/32 606/66 |
| 5,318,570 A | * | 6/1994 | Hood | A61B 17/8847 601/2 |

(Continued)

*Primary Examiner* — Zade Coley
(74) *Attorney, Agent, or Firm* — Oliff PLC

(57) ABSTRACT

A method for replacement arthroplasty of an embodiment is losing precise cutting and surface unevenness and performing the smoothening treatment to the part of the joint region which the component of the artificial joint attaches, using an ultrasonic treatment device, and exact processing can be performed, dimensional processing accuracy also becomes high, and bonding surfaces stick it without a crevice, and it controls generating of wear debris by friction.

7 Claims, 10 Drawing Sheets

(56) References Cited

U.S. PATENT DOCUMENTS

| | | | | |
|---|---|---|---|---|
| 5,344,460 A * | 9/1994 | Turanyi | ............... | A61F 2/389 623/20.33 |
| 5,382,251 A * | 1/1995 | Hood | ............. | A61B 17/8847 606/2 |
| 5,733,119 A * | 3/1998 | Carr | ................. | A61C 1/07 433/102 |
| 8,273,087 B2 * | 9/2012 | Kimura | ............... | A61B 17/16 606/169 |
| 2002/0065518 A1 * | 5/2002 | Naybour | ............ | A61F 2/4601 606/86 R |
| 2002/0193797 A1 * | 12/2002 | Johnson | ............ | A61B 17/1628 606/79 |
| 2003/0220698 A1 * | 11/2003 | Mears | ............. | A61B 17/00234 623/22.4 |
| 2005/0177172 A1 * | 8/2005 | Acker | ............ | A61B 17/00234 606/99 |
| 2009/0287309 A1 * | 11/2009 | Walch | ................ | A61B 17/15 623/18.11 |
| 2009/0318944 A1 * | 12/2009 | Kimura | ............... | A61B 17/16 606/169 |
| 2013/0226189 A1 * | 8/2013 | Young | ............... | A61F 2/4607 606/99 |

\* cited by examiner

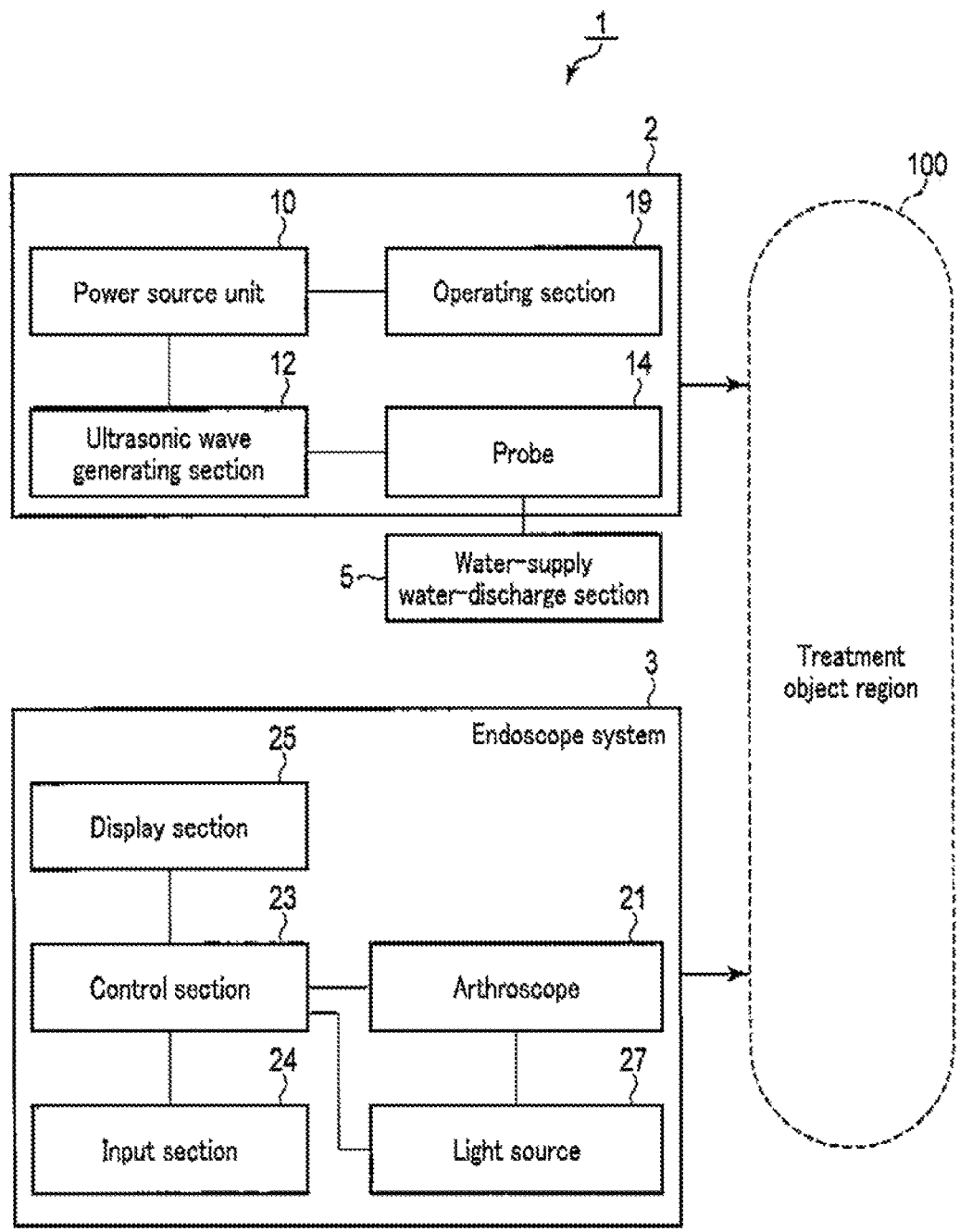
F I G. 1

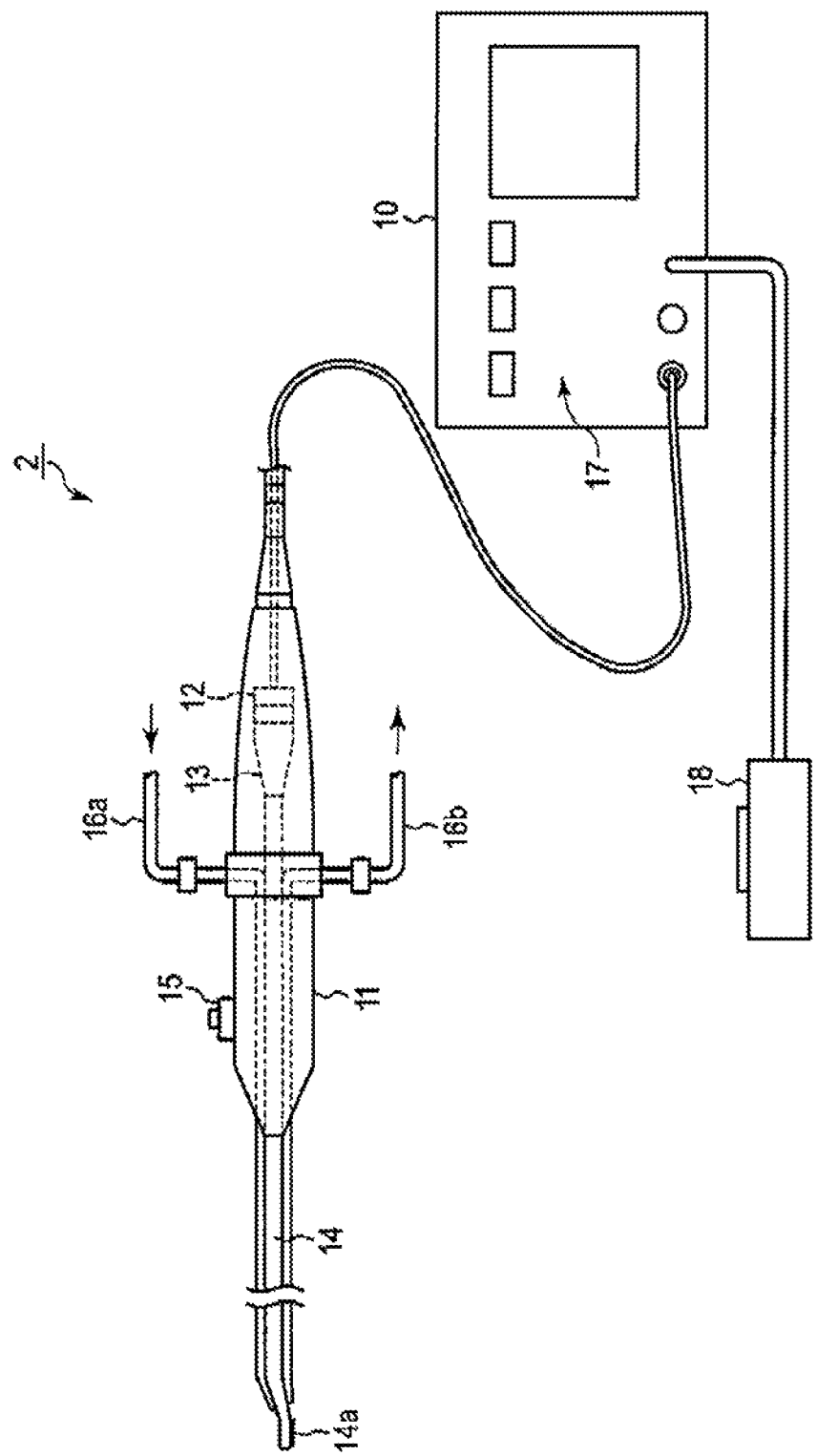
F I G. 2

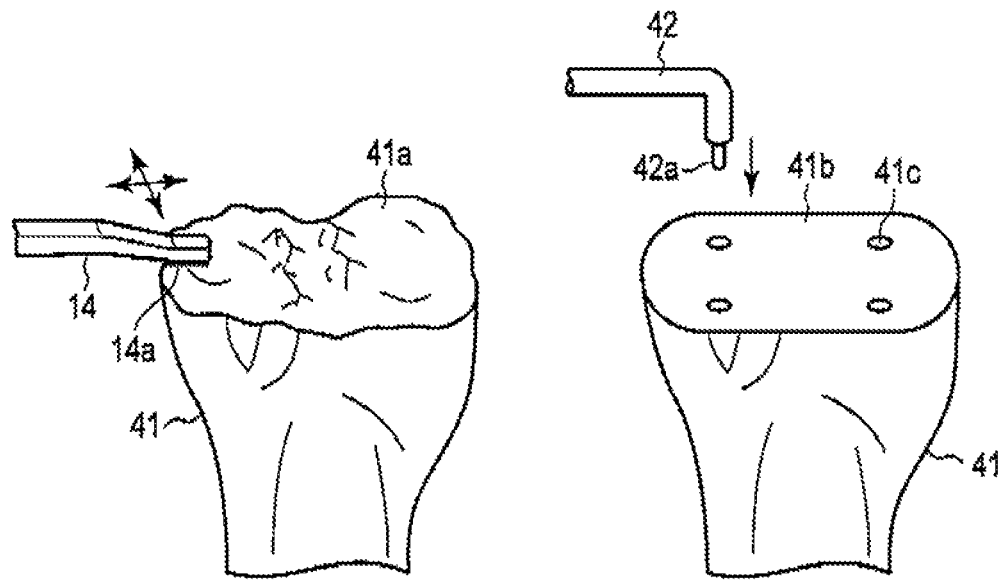
F I G. 4A    F I G. 4B
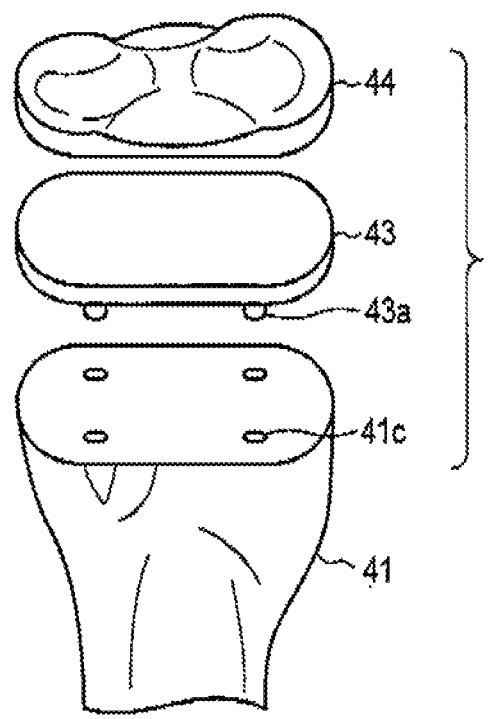
F I G. 4C

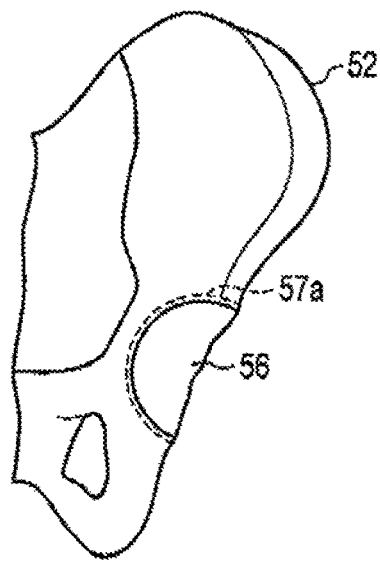
F I G. 9A
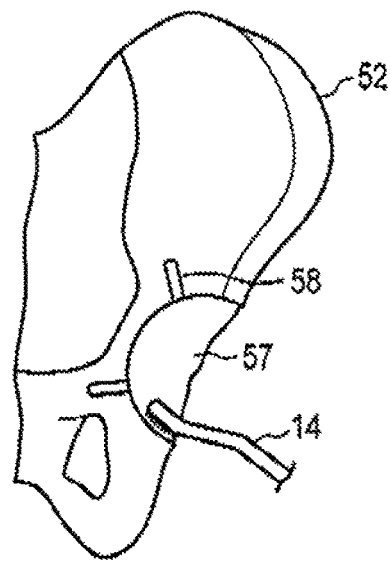
F I G. 9B
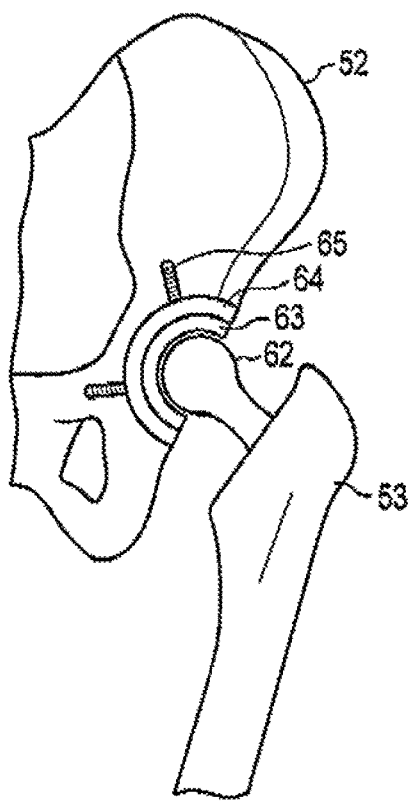
F I G. 10

METHOD FOR REPLACEMENT ARTHROPLASTY

CROSS-REFERENCE TO RELATED APPLICATIONS

This application is based upon and claims the benefit of priority from the prior U.S. Provisional Application No. 62/268,931 filed Dec. 17, 2015, the entire contents of which are incorporated herein by reference.

BACKGROUND OP THE INVENTION

1. Field of the Invention

The present invention relates to a method for replacement arthroplasty to prepare an artificial joint by use of an ultrasonic treatment device.

2. Description of the Related Art

In general, an artificial joint wears away and loosens due to long use. When this looseness is generated, a replacement operation is required again. However, when a user is very old, the user might hesitate to undergo the operation again in consideration of rehabilitation and the like.

In a case where this artificial joint is, for example, an artificial hip joint, a stem is disposed in a femur. In this case, the femur is cut into a shape to receive the stem (a material of the stem is usually a metal material such as a titanium alloy) with a drill or the like, but in this technique, accuracy of a cut surface is not much high. In a case where the accuracy is low, a clearance is present between the stem and the bone when the stem is attached, and hence friction is generated together with the looseness. Due to this friction, wear debris of the material might be generated. A situation (called bone absorption) occurs in which the worn material is recognised as a foreign matter on a biological side to cause a biological reaction, thereby melting the bone around the artificial joint, and it is considered that this situation increases the clearance around the stem of the artificial joint.

To eliminate such a problem, there is provided a technique to dispose an artificial joint that is hard to loosen even when the artificial joint is used for a long period of time. Furthermore, the technique can contribute to decrease of occurrence of pain, because the artificial joint less loosens.

BRIEF SUMMARY OF THE INVENTION

According to an embodiment of the present invention, there is provided a method for replacement arthroplasty comprising; a step of cutting out at least one attaching surface of a bone constituting a joint, by use of a treating section disposed at a distal end of a probe of an ultrasonic treatment device and ultrasonically vibrated; a reaming step of performing a reaming treatment for the attaching surface cut out of the bone, by use of the treating section disposed at the distal end of the probe and ultrasonically vibrated; and a rasping step of performing a rasping treatment for the surface cut out of the bone in the step of cutting out the attaching surface, by use of the treating section disposed at the distal end of the probe and ultrasonically vibrated.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a diagram showing a constitution example of a surgical system comprising an ultrasonic treatment device to carry out replacement arthroplasty of the present embodiment;

FIG. 2 is a view showing a constitution example of the ultrasonic treatment device in the present surgical system;

FIG. 4A is a view showing a state of cutting a tip of a tibia;

FIG. 4B is a view showing a state of forming a tip off the tibia in a bonding surface of a base plate;

FIG. 4C is a view of an assembly of the base plate and an articular facet surface which are to be attached to the tibia;

FIG. 9A is a view showing an acetabulum of the pelvis that becomes a receiving port oaf the femur component;

FIG. 9E is a vie of performing a smoothening treatment of the acetabulum by use of the ultrasonic treatment device;

FIG. 10 is a view showing a state where the femur component is attached to the pelvis.

DETAILED DESCRIPTION OF THE PREFERRED EMBODIMENTS

Figure 3A:
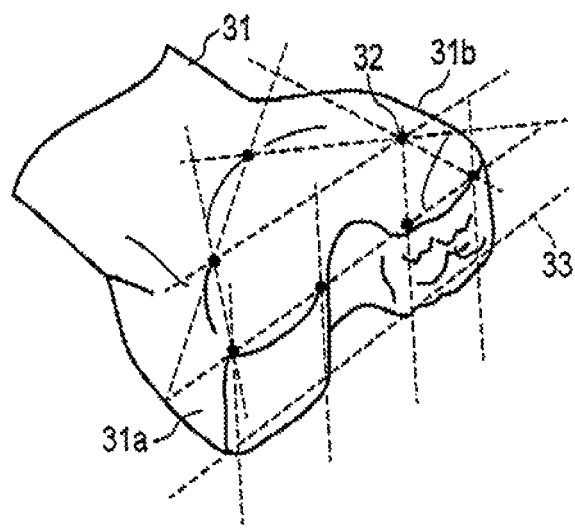
FIG. 3A is a view showing positional information of an attaching surface to attach, to a femur, a U-shaped implant that becomes an artificial knee joint.

Hereinafter, with reference to the drawings, there will be described a method for replacement arthroplasty to prepare an artificial joint according to an embodiment of the present invention. In the following respective embodiments, there will be described two examples where treatment target regions are a knee joint and a hip joint, but the regions are not limited to these joints, and it is also possible to easily carry out a surgery for another joint by use of an ultrasonic treatment device in the same manner.

FIG. 1 shows a constitution example of a surgical system comprising the ultrasonic treatment device to carry out replacement arthroplasty of the present embodiment. FIG. 2 is a view showing a constitution example of the ultrasonic treatment device in the present surgical system.

A surgical system 1 of the resent embodiment is constituted of an ultrasonic treatment device 2 an endoscope system 3 including an arthroscope 21, and a water-supply water-discharge section 5 that supplies end discharges perfusion such as saline.

The ultrasonic treatment device 2 comprises an ultrasonic wave generating section 12 that generates ultrasonic vibration by an ultrasonic vibration element (e.g., a piezoelectric element), a probe 14 that transmits the ultrasonic vibration to perform a cutting treatment of the treatment target region, a power source unit 10 that supplies a driving power to the ultrasonic wave generating section 12, and an operating section 19 to perform an on/off operation of the generation of the ultrasonic vibration. By the ultrasonic treatment device 2, a cutting treatment and an incising treatment are performed to treatment target regions such as a biological tissue, a cartilage and a bone (a subchondral bone) by use of the ultrasonic vibration.

The water-supply water-discharge section 5 supplies perfusion such as the saline to a periphery of a treatment object region 100 including a joint through the ultrasonic treatment device 2, discharges the perfusion from the periphery, and thus circulates the perfusion at a constant flow rate. In the present embodiment, the supplying and discharging are performed through the water-supply water-discharge section 26, but the supplying and discharging may be performed through the endoscope system 3.

The endoscope system 3 is constituted of the arthroscope 21 made of a hard mirror that is one type of endoscope, a visible light source 27 that is a light source of illumination light for irradiation with the illumination light of visible light, control section 23 that controls the whole endoscope system 3, an input section 24 such as a keyboard or a touch panel, and a display section 25 that displays surgical information including a photographed surgical situation.

The ultrasonic treatment device 2 of the present embodiment will be described in detail.

As shown in FIG. 2, the ultrasonic treatment device 2 of the present embodiment is constituted of a treatment device main body 11 comprising the ultrasonic wave generating section 12 and the probe 14, the power source unit 10, and a foot switch 18 that instructs the on/off operation of the generation of the ultrasonic vibration. The treatment device main body 11 is connected to the power source unit 10 via a cable, thereby performing the supply of the driving power and communication of a control signal.

The treatment device main body 11 comprises the ultrasonic wave generating section 12 having a tubular shape to be grasped by an operator and including therein, an ultrasonic vibrator (a piezoelectric member or the like), the thin and long probe 14 having its proximal side acoustically connected to the ultrasonic wave generating section 12 via a horn 13, a treating section 14a disposed at a distal end of the probe to perform cutting, an operation switch 15 disposed on the treatment device main body 11 to instruct the on/off operation of the generation of the ultrasonic vibration, and flow channels 16a and 16b to supply and discharge the perfusion from the water-supply water discharge section 5 to circulate the perfusion. The foot switch 11 has a function identical to that of the operation switch 15.

Although not shown, the treating section 14a is provided with projections having edges, the cartilage can be cut off by the edges, and the cartilage can be melted and cut off by friction heat generated between the treating section 14 and the cartilage. Additionally, bones (a cortical bone and a cancellous bone) such as the subchondral bones can be hammered with the above-mentioned projections of the treating section 14a by use of the ultrasonic vibration in the same manner as in a hammer (hammering), and the bone can remarkably finely be ground and cut off.

First Embodiment

Next, with reference to FIG. 3A, FIG. 3B and FIG. 4A to FIG. 4D, there will be described a method for replacement arthroplasty of an artificial knee joint according to a first embodiment. FIG. 3A is a view showing positional information of an attaching surface to attach, to a femur, a U-shaped implant that becomes the artificial knee joint, FIG. 33 is a view showing a state of attaching the implant to the attaching surface of the femur, and FIG. 3C is a view showing a state where the implant is attached to the femur. FIG. 4A is a view showing a state of cutting a tip of a tibia, FIG. 4B is a view showing a state of forming the tip of the tibia in a bonding surface of a base plate, and FIG. 4C is a view of an assembly of the base plate and an articular facet surface which are to be attached to the tibia.

This artificial knee joint comprises two joint coupled regions, and is constituted of a femur implant 34 that becomes a first joint portion to be attached to a femur, and a base plate 43 and an articular facet surface 44 which constitute an attaching portion of a tibia implant and become a second joint portion to be attached to the tibia.

First, as shown in FIG. 3A, an attaching surface is positioned to tips 31a and 31 of a femur 31 to correspond to an attaching dimension of the femur implant to be attached (step S1). For this positioning setting, the positioning is performed by measuring an actual dimension of the femur 31 or actually bringing the femur implant into contact with the femur, and the femur is directly marked by using the ultrasonic treatment device 2. Furthermore, an image of the imaged femur 31 and information such as the attaching dimension of the femur implant 34 may be input into a personal computer to set a position of the attaching surface of the femur 31 on the image by image processing, and the femur may directly be marked by using the ultrasonic treatment device 2.

Figure 3B:
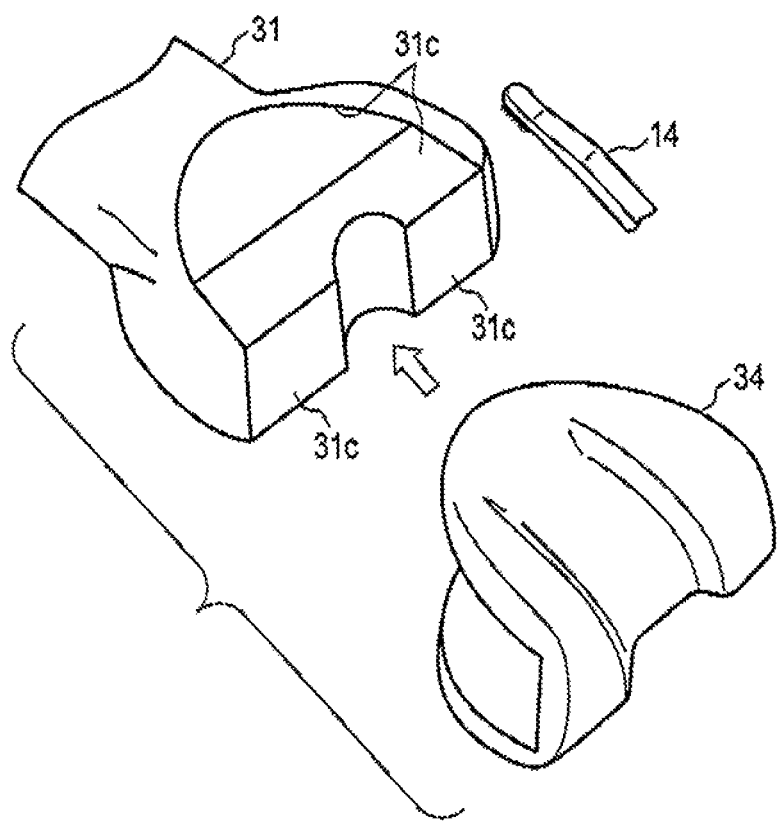
FIG. 3B is a view showing a state of attaching the implant to the attaching surface of the femur.
Figure 3C:
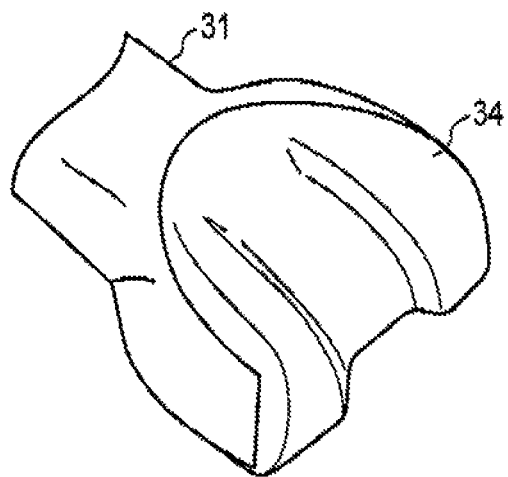
FIG. 3C is a view showing a state where the implant is attached to the femur.

Next, as shown in FIG. 3B, under a situation in which the perfusion circulates, the tip of the femur is cut and formed to match an attaching surface of the femur implant 34, in accordance with the above-mentioned positioning setting by use of the ultrasonic treatment device 2 (step S2). At this time, the femur 31 is roughly cut into an approximate size that is larger than the attaching dimension of the femur implant 34, and then the femur may finely be adjusted by bringing the femur implant 34 into contact with the femur.

Furthermore, each cut surface 31c of the femur 31 and the attaching surface of the femur implant are flattened and finished to eliminate unevenness from the surfaces by use of the ultrasonic treatment device 2 (step S3). Through this flattening, the surfaces come in contact closely with each other and are fixed with increased strength at a time of attaching. In such an excising treatment of the tip of the femur, the tip of the femur can smoothly be excised with small force by use of the ultrasonic vibration of the ultrasonic treatment device, so that handling can easily be performed and the tip can accurately be excised along an intended line.

Next, as shown in FIG. 3C, the femur implant 34 is attached to the attaching surfaces 31c of the femur 31 and fixedly bonded thereto by use of an adhesive (step 34). The femur implant 34 may have a screwing fixing structure in which screws or the like are used.

Next, as shown in FIG. 4A, a tip of a tibia 41 is flatly cut by using the ultrasonic treatment device 2 under the situation in which the perfusion circulates (step S5). Furthermore, a reaming treatment of a cutting and shaping treatment and a rasping treatment of a polishing treatment are successively performed, and an attaching surface 41b that becomes a receiving region of the base plate 43 is formed in the tibia 41 to match a shape of the bonding surface of the base plate made of a metal (step S6).

On the bonding surface (a back surface side) of the base plate 43 of the attaching portion of tibia implant applied to the present embodiment, anchors 43a comprising four cylindrical projections disposed. As shown in FIG. 4B, cylindrical concave regions 41c to fit with the anchors 43a are formed in the attaching surface 41b of the tibia 41 (step S7). The concave regions 41c are formed by using the ultrasonic treatment device 2 in which an L-shaped probe 42 comprises a treating section 42a having a diameter equal to or smaller than that of the anchor 43a and including a pointed end portion that is bent in its middle and has a pointed distal end. The treating section 42a is pressed against the surface in a direction intersecting a longitudinal direction of the probe 42 to make a hole by cutting the surface. Therefore, the treating section is suitable for a case where a space to perform the cutting is narrow, or the like.

The probe 42 has the shape bent at a right angle, but a bending angle is not limited to the right angle and may be any angle. Additionally, the probe does not have to be necessarily bent, and may comprise the treating section 42a extending in the same direction as the longitudinal direction of the probe 42. In this case, the probe 42 is held vertically to the attaching surface 41b of the tibia 41 and pressed against the surface in a vertical direction to make the hole by the cutting.

The anchors 43a are fitted into the concave regions 41c and the base plate 43 is fixed to the tip of the tibia 41 via the adhesive (step S8). It is to be noted that as means for fixing the base plate 43 to the attaching surface 41b of the tibia 41, the screwing fixing structure using the screws or the like may be used.

Next, the articular facet surface 44 made of a resin is inserted into a surface side of the base plate and fixed thereto (step S9). Although not shown, the articular facet surface and the bonding surface of the base plate are beforehand constituted to be fittable with each other. It is to be noted that a structure other than the fitting structure may be used and, for example, fixing by use of the adhesive may be performed.

In the present embodiment, the attaching surface 41b of the tibia 41 is processed by using the ultrasonically vibrated treating section 14a of the probe 14 of the ultrasonic treatment device 2, whereby a flat surface having remarkably less unevenness can more accurately be formed as compared with processing by a conventional treatment tool such as a bar ablator. Furthermore, when the attaching surface 41b is the accurately flat surface, positional accuracy of the concave regions 41c to the anchors 43a of the base plate 43 also increases.

In consequence, dimensional accuracy of the positioning of the base plate 43 increases, close contact properties between the attaching surface 41b and the bonding surface of the base plate 43 enhance, a clearance is harder to be generated than before, and possibilities of generation of friction can be decreased. Therefore, the fixing of the base plate 43 to the tibia 41 strengthens, looseness is hard to be generated, and longer use is enabled.

Second Embodiment

Figure 5:
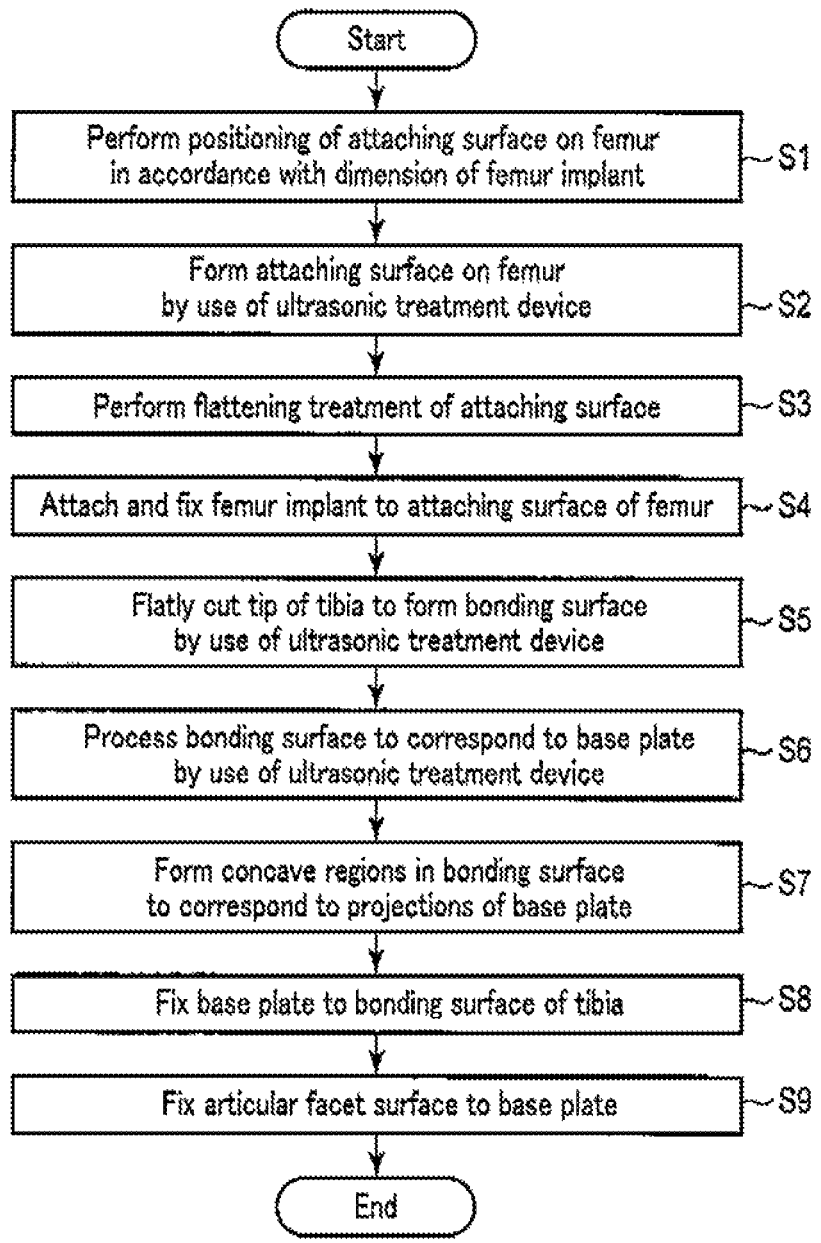
FIG. 5 is a flowchart to explain surgical steps of a method for replacement arthroplasty of an artificial hip joint.
Figure 6:
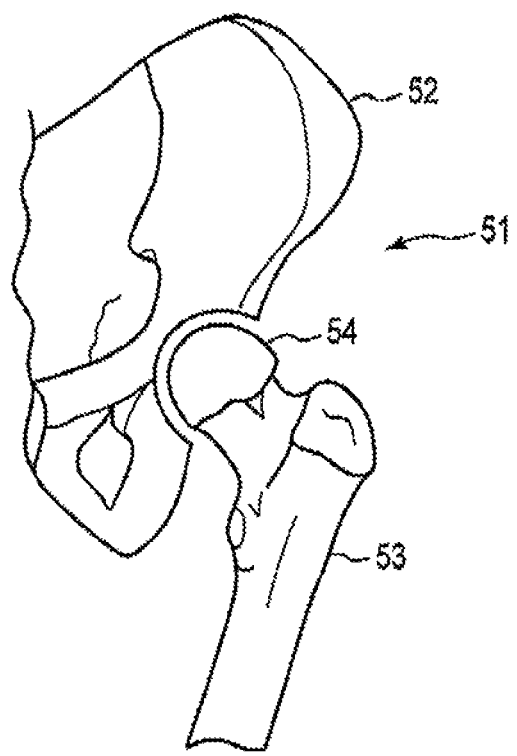
FIG. 6 is a view snowing a pelvis and a femur which become targets of a replacement operation.
Figure 7A:
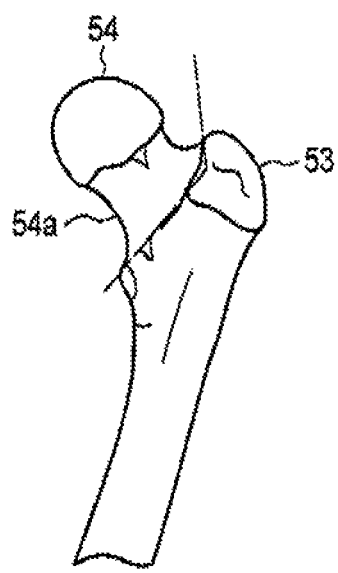
FIG. 7A is a view to explain severance of the femur.
Figure 7B:
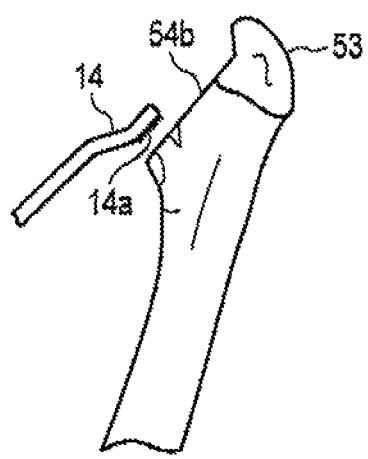
FIG. 7B is a view showing a state of a flattening treatment of the attaching surface.
Figure 7C:
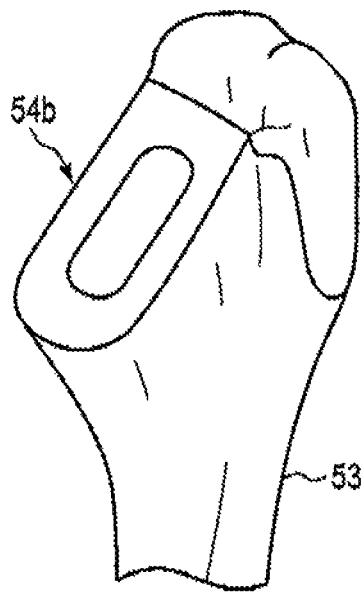
FIG. 7C is a view showing the flattened attaching surface.
Figure 7D:
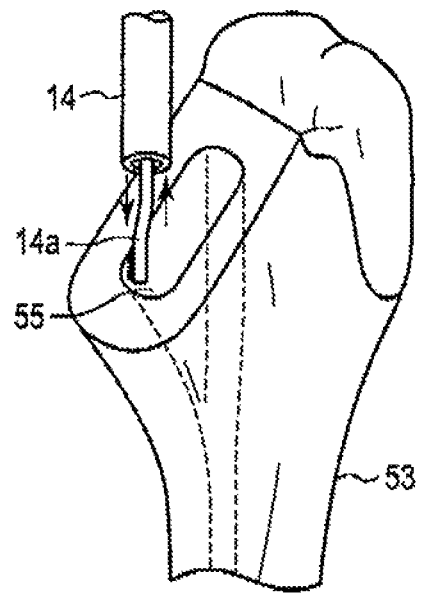
FIG. 7D it a view showing a state of forming a medullary cavity of the femur in a stem attaching hole by use of an ultrasonic treatment device.
Figure 8:
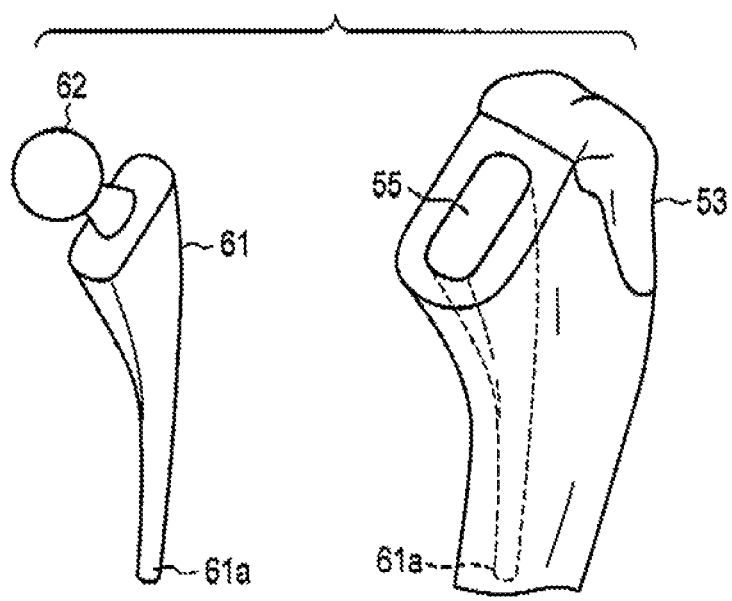
FIG. 8 is a view show appearances of a femur component and the femur in which the medullary cavity is formed.
Figure 11:
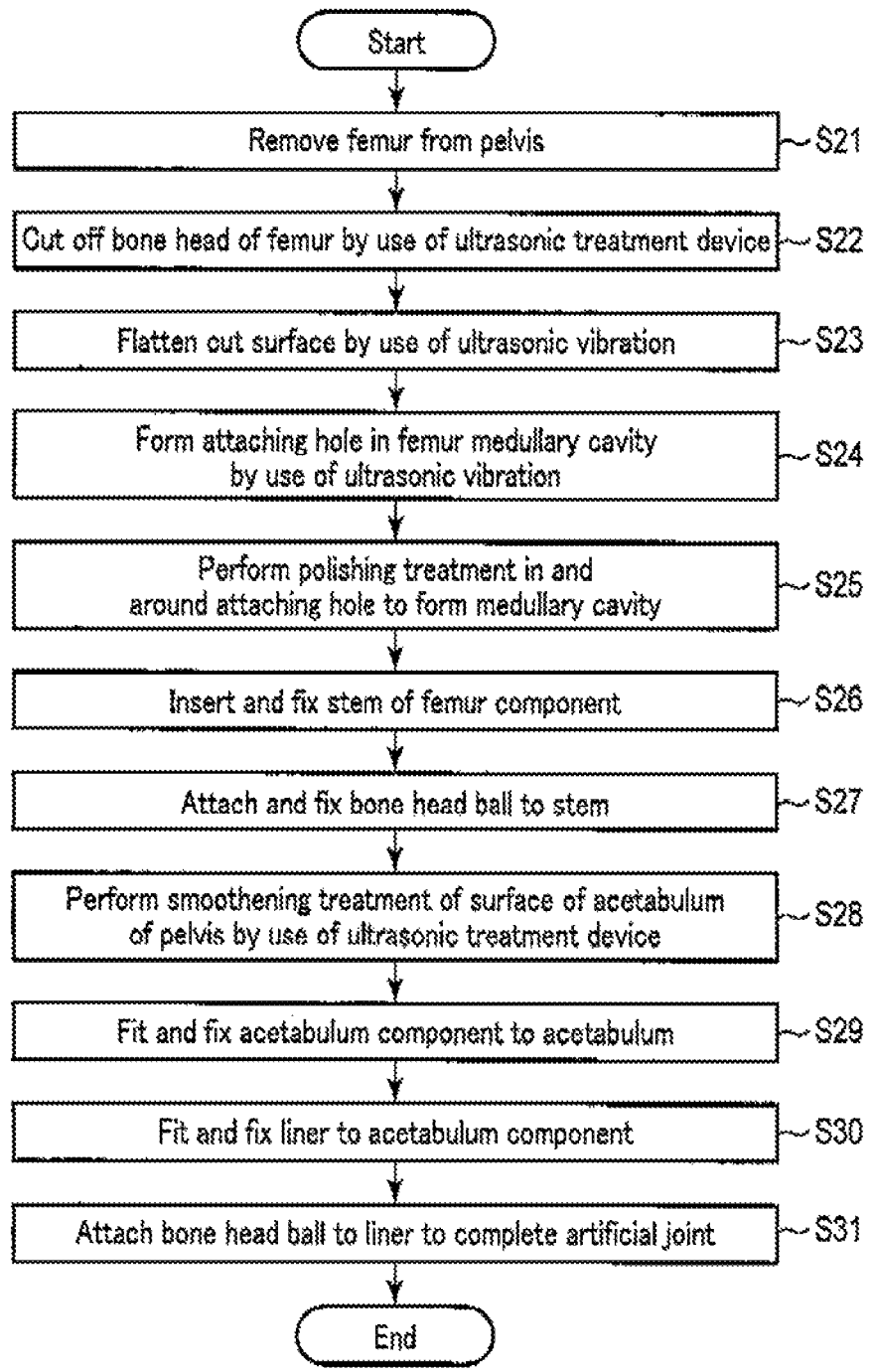
FIG. 11 is a view to explain surgical steps of the method for the replacement arthroplasty of the artificial hip joint.

Next, with reference to surgical steps in FIG. 5, FIG. 6, FIG. 7A to FIG. 7D, and FIG. 8 to FIG. 11, there will be described a method for replacement arthroplasty of an artificial hip joint according to a second embodiment. FIG. 5 is a flowchart to explain surgical steps of the method for the replacement arthroplasty of the artificial hip joint. FIG. 6 is a view showing a pelvis and a femur which become targets of a replacement operation. FIG. 7A is a view to explain severance of the femur, FIG. 7B is a view showing a state of a flattening treatment of an attaching surface, FIG. 7C is view showing the flattened attaching surface, and FIG. 7D is a view showing a state of forming a medullary cavity of the femur in a stem attaching hole by use of an ultrasonic treatment device. FIG. 8 is a view showing appearances of a femur component and the femur in which the medullary cavity is formed. FIG. 9A is a view showing an acetabulum of the pelvis which becomes a receiving port of the femur component, and FIG. 9B is a view showing a state of performing a flattening treatment of the acetabulum by use of the ultrasonic treatment device. FIG. 10 is a view showing a state where the femur component is attached to the pelvis. FIG. 11 is a view to explain surgical steps of the method for the replacement arthroplasty of the artificial hip joint.

FIG. 6 conceptually shows an original hip joint region 51 to which the artificial hip joint is attached. A clearance is generated between an acetabulum of a pelvis 52 and a bone head of a femur 53. First, in an excising step of the bone head, the femur is removed from the pelvis in a deformed joint region (step S21). Next, a position to cut off a bone head 54 of the femur 53 is set. In the present embodiment, as shown in FIG. 7A, a cutting line connecting a lesser trochanter to a greater trochanter is set in a boundary between a femur body and a femur neck 54a.

Afterward, under a situation in which perfusion circulates, the bone head 54 is excised along the set cutting line by use of an ultrasonic treatment device 2 (step S22). This excision can smoothly be performed with smaller force by use of ultrasonic vibration, handling is therefore easily performed, and furthermore, the excision along the intended line can easily be performed. Furthermore, as shown in FIG. 7B and FIG. 7C, unevenness of a cut surface 54b is eliminated and the surface is flattened with a treating section 14a of a probe 14 of the ultrasonic treatment device 2, so that the cut surface becomes a flat surface (step 323).

Next, as shown in FIG. 7D, under the situation in which the perfusion circulates, an inner surface of a femur medullary cavity 55 is cut with the ultrasonically vibrated treating section 14a of the probe 14, and an attaching hole, into which a stem 61 is fittable, is formed (a reaming treatment) (step S24). Furthermore, a polishing treatment, i.e., a rasping treatment is performed in and around the formed attaching hole (step S25). The ultrasonic treatment device 2 is used in this treatment, whereby the surface can accurately be finished to obtain a noticeably smoother surface as compared with conventional surface roughness. Furthermore, the surface can be formed to match an appearance shape of the stem 61 and come in contact closely with the stem, and a clearance can be prevented from being generated between the stem 61 and the attaching hole.

Next, a tip 61a of the stem 61 that is the femur component is inserted into the attaching hole and fixed thereto (step S26). Furthermore, a bone head ball 62 is attached and fixed to a support base of the stem 61 (step S27).

Next, the treatment shifts to a treatment of an acetabulum 56 on a pelvis side which becomes a receiving port of the bone head ball 62. As shown in FIG. 9A, under the situation in which the perfusion circulates, the flattening treatment to smoothen the surface of the acetabulum 56 is performed so that an acetabulum comment 64 can be attached to acetabulum 56 in which a defect on the pelvis side is generated, by use of the ultrasonic treatment device 2. Furthermore, as shown in FIG. 9B, screw holes 58 are formed and a receiving port 57 on the pelvis side is formed (step S28). Next, the acetabulum component 64 is fitted into the port and fixed thereto by using screws 65 (step S29), and a cup-shaped liner 63 of the artificial joint fitted and fixed to the acetabulum component 64 (step S30).

As shown FIG. 10, the bone head ball 6 fixed to the stem 61 is attached to the liner 63 on the pelvis side, thereby completing the artificial hip joint (step S31).

For the above-mentioned method for the replacement arthroplasty of the artificial hip joint of the present embodiment, the ultrasonic treatment device 2 is used in the treatment device for the formation of the femur medullary cavity 55 of the femur 53 shown in FIG. 7D, so that it is possible to obtain smooth surfaces as the medullary cavity inner surface and the cut surface 54a at accuracy noticeably higher than processing accuracy in a case where a conventional treatment tool is used. Therefore, the medullary cavity inner surface and the cut surface become the accurately smoothened surfaces, thereby increasing accuracy of an attaching dimension, and a clearance between the stem 61 and the medullary cavity inner surface is harder to be generated than before. As a result, there decrease possibilities of generation of friction due to rubbing of the stem 61 and the medullary cavity inner surface against each other, and it is possible to inhibit bone absorption in which a bone around the stem is melted.

Therefore, even when the artificial hip joint is attached and used for a long period of time, the generation of the clearance is inhibited, and looseness is hard to be generated.

In the formation of the acetabulum 57 shown in FIG. 9B, a smoothening treatment of the surface of the acetabulum 56 in which the defect is generated is performed by using the ultrasonic treatment device 2, and hence the acetabulum component 64 can more accurately be attached at a higher fitting degree of the component as compared with conventional processing. The treating section 14a of the distal end of the probe 14 may have a spherical surface or a ball shape as long as the surface of the acetabulum 57 is cut in the treatment. It is to be noted that although not shown, small dimpled holes are suitably formed in the spherical surface or the surface of the ball shape.

According to the present embodiment, the smoothening treatment is performed by using the ultrasonic treatment device to increase the dimensional accuracy of the medullary cavity of the femur and the receiving port on the pelvis side (the acetabulum) and smoothen these surfaces, and hence the artificial joint can be attached to the pelvis and the femur without any clearances.

An ultrasound frequency of the ultrasonic treatment device in the present embodiment is transmitted at a frequency of, for example, 47 KHz, 23.5 KHz or the like. Additionally, an amplitude of the ultrasonic vibration is preferably from 50 μm to 200 μm. Furthermore, the ultrasound frequency and amplitude might be set to values other than the above values in accordance with design/specifications of the ultrasonic treatment device.

In the ultrasonic treatment device for use in the present embodiment, a treatment device main body containing the ultrasonic vibrator, the horn and the like is formed into a compact size that can easily be held in a hand. The treatment target region, e.g., the bone can be incised and cut by ultrasonically vibrating the distal end of the probe of the treatment device main body which is pressed against the bone.

The ultrasonic vibration is finely and continuously generated at a high rate, whereby the excised surface can be prepared in the for of a noticeably precisely excised surface having less unevenness as compared with a conventional excision technique.

Furthermore, the ultrasonic treatment device for use in the present embodiment quietly vibrates as compared with the conventional treatment tool, and hence the processing can exactly be performed and dimensional processing accuracy can be increased. Consequently, affinity for an implant improves, generation of wear debris due to the friction can be inhibited, and additionally, looseness of the implant itself can be inhibited, so that the artificial joint is usable longer than before.

Furthermore, in the bone excision in which the ultrasonic vibration is used, it is possible to cut the bone at noticeably high accuracy as compared with a drill, a shaver, a bar ablator or the like heretofore used in the method for the replacement arthroplasty. Additionally, the bone can not only be out but also be shaved on by lightly attaching the ultrasonic treatment device against the bone, and hence the flattening or smoothening of the surface can easily be achieved. Therefore, the artificial joint can accurately be attached, generation of a worn material during the long use can be prevented, looseness can be inhibited, and longer use of the artificial joint is enabled.

Furthermore, there has been described the case where the cutting or surface polishing of the attaching surface to which the portion of the artificial joint is attached is performed by using the ultrasonic treatment device for the above-mentioned knee joint and hip joint, but the ultrasonic treatment device used for the artificial hip joint is easily applicable to a method for replacement arthroplasty of an artificial shoulder joint. For example, by using the ultrasonic treatment device, there is performed a reaming treatment or a rasping treatment of a receiving region in a humerus to attach an upper arm implant, or a reaming treatment or a rasping treatment to attach a glenoid to a scapula side.

The above-mentioned present embodiment also it includes the following gist.

(1) There is provided an ultrasonic method for placement arthroplasty which is performed by using a system comprising an ultrasonic transmitter (a power source device), an ultrasonic vibrator and an ultrasonic probe, further comprising water supply means and being capable of supplying water from a probe distal end. In consequence, when bone excision/formation is performed by using ultrasonic vibration, effects of heat which could be generated can be decreased.

(2) There is provided an ultrasonic method for replacement arthroplasty which comprises an ultrasonic transmitter (a power source device), an ultrasonic vibrator and an ultrasonic probe, and in which at a time of formation of a medullary cavity, bone excision/formation is performed under water while filling the medullary cavity with the water. In consequence, when the bone excision/formation is performed by using ultrasonic vibration, generated heat effects can be decreased.

(3) There is provided an ultrasonic method for replacement arthroplasty which comprises an ultrasonic transmitter power source device), an ultrasonic vibrator, an ultrasonic probe and an arthroscopic system, and in which at a time of formation of a medullary cavity, bone excision/formation is performed under water while confirming an excised region with an arthroscope. When the bone excision/formation s performed by using ultrasonic vibration, it is possible to decrease heat effects which could be generated and to more exactly and securely perform the excision.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. A method for replacement arthroplasty comprising:
   determining on a femur a position of a first attaching surface to be formed in the femur to receive a femur implant under a situation in which a perfusion circulates;
   forming the first attaching surface in the femur by using a treating section disposed at a distal end of a probe of an ultrasonic treatment device and ultrasonically vibrated under the situation in which the perfusion circulates;
   fixing the femur implant to the first attaching surface of the femur;
   forming a second attaching surface in a tibia of a joint with the femur to receive a base plate by using the treating section of the probe of the ultrasonic treatment device under the situation in which the perfusion circulates;
   performing a reaming treatment, as a first treatment for the second attaching surface, by using the treating section of the probe of the ultrasonic treatment device under the situation in which the perfusion circulates;
   performing a rasping treatment, as a second treatment for the second attaching surface treated by the reaming treatment, by using the treating section of the probe of the ultrasonic treatment device under the situation in which the perfusion circulates;
   forming a plurality of concave regions in the second attaching surface by using a pointed end portion disposed at the distal end of the probe of the ultrasonic treatment device and ultrasonically vibrated under the situation in which the perfusion circulates; and
   fixing the base plate to the tibia by fitting anchors of the base plate into the plurality of concave regions.

2. The method for the replacement arthroplasty according to claim 1, wherein:
   the concave regions are formed by using the treating section;
   the treating section has a diameter equal to or smaller than that of the anchors;
   the pointed end portion is bent in its middle; and
   the concave regions are formed in a manner to extend in a direction intersecting a longitudinal direction in which the treatment device is inserted.

3. The method for replacement arthroplasty according to claim 1, further comprising fixing an articular facet surface to the base plate, the articular facet surface forming an artificial joint by coming in contact with the femur implant.

4. The method for replacement arthroplasty according to claim 1,
   wherein:
   the determining on a femur the position of the first attaching surface to be formed in the femur to receive a femur implant comprises determining the position to correspond to an attaching dimension of the femur implant and marking the position on the femur by use of the treating section disposed at the distal end of the probe of the ultrasonic treatment device and ultrasonically vibrated; and
   the forming the first attaching surface in the femur comprises, based on the marked position, (1) cutting out a portion of bone of the femur by pressing the treating section against the bone of the femur and using ultrasonic vibration and (2) pressing the treating section against cartilage of the femur and melting and cutting the cartilage by friction heat generated by ultrasonic vibration.

5. A method for replacement arthroplasty comprising:
   determining a position on a femur under a situation in which a perfusion circulates;
   removed from a hip joint for cutting off a bone head of the femur;
   cutting off the bone head at the position by use of a treating section disposed at a distal end of a probe of an ultrasonic treatment device and ultrasonically vibrated, forming a cut surface on the under the situation in which the perfusion circulates;
   performing a flattening treatment on the cut surface under the situation in which the perfusion circulates;
   forming an attaching hole in the femur for a femur component to be inserted by use of the treating section of the probe of the ultrasonic treatment device under the situation in which the perfusion circulates; and
   inserting and fixing a tip of a stem of the femur component including a bone head ball into the attaching hole.

6. The method for replacement arthroplasty according to claim 5, wherein the forming the attaching hole in the femur comprises:
   performing a reaming treatment to shave an inner surface of a medullary cavity of the femur by use of the treating section of the ultrasonic treatment device; and
   performing a rasping treatment to the attaching hole treated by the reaming treatment.

7. The method for replacement arthroplasty according to claim 5, further comprising:
   performing a flattening treatment to a surface of an acetabulum on a pelvis side from which the femur is removed by use of the treating section of the ultrasonic treatment device;
   fitting and fixing an acetabulum component to the acetabulum treated by the flattening treatment;
   fitting and fixing a cup-shaped liner of an artificial joint to the acetabulum component; and
   attaching the femur to a hip joint by attaching the bone head ball to the liner.

* * * * *